(12) United States Patent
Satou et al.

(10) Patent No.: US 6,717,666 B2
(45) Date of Patent: Apr. 6, 2004

(54) METHOD AND APPARATUS FOR MEASURING NITROGEN IN A GAS

(75) Inventors: Tetsuya Satou, Tokyo (JP); Shang-Qian Wu, Tokyo (JP); Tetsuya Kimijima, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 10/098,451

(22) Filed: Mar. 18, 2002

(65) Prior Publication Data

US 2002/0140932 A1 Oct. 3, 2002

(30) Foreign Application Priority Data

Mar. 29, 2001 (JP) .......................... 2001-097154
Jun. 19, 2001 (JP) .......................... 2001-184908

(51) Int. Cl.[7] ............................................. G01N 21/69
(52) U.S. Cl. .......................... 356/311; 356/316
(58) Field of Search ................................ 356/311, 316, 356/417, 313, 314

(56) References Cited

U.S. PATENT DOCUMENTS

| 3,032,654 A | * | 5/1962 | Fay et al. .................. 250/373 |
| 5,412,467 A | * | 5/1995 | Malczewski et al. ....... 356/316 |
| 6,043,881 A | * | 3/2000 | Wegrzyn et al. ............ 356/316 |

FOREIGN PATENT DOCUMENTS

JP          11326219          11/1999

* cited by examiner

*Primary Examiner*—F. L. Evans
(74) *Attorney, Agent, or Firm*—Roylance, Abrams, Berdo & Goodman, L.L.P.

(57) ABSTRACT

The present invention provides a method and an apparatus for analyzing nitrogen in a gas, in which the concentration of nitrogen can be continuously measured with good sensitivity without wasting a sample gas.

At least one wavelength for measuring a concentration of nitrogen according to the intensity of a light generated by discharge, is selected from a group consisting of 215±2 nm, 226±2 nm, 238±2 nm, 242±2 nm, 246±1 nm, 256±2 nm, 260±2 nm, 266±2 nm, 271±1 nm, 276±4 nm, 285±2 nm, 294±1 nm, and 300±2 nm.

19 Claims, 12 Drawing Sheets

FIG.3
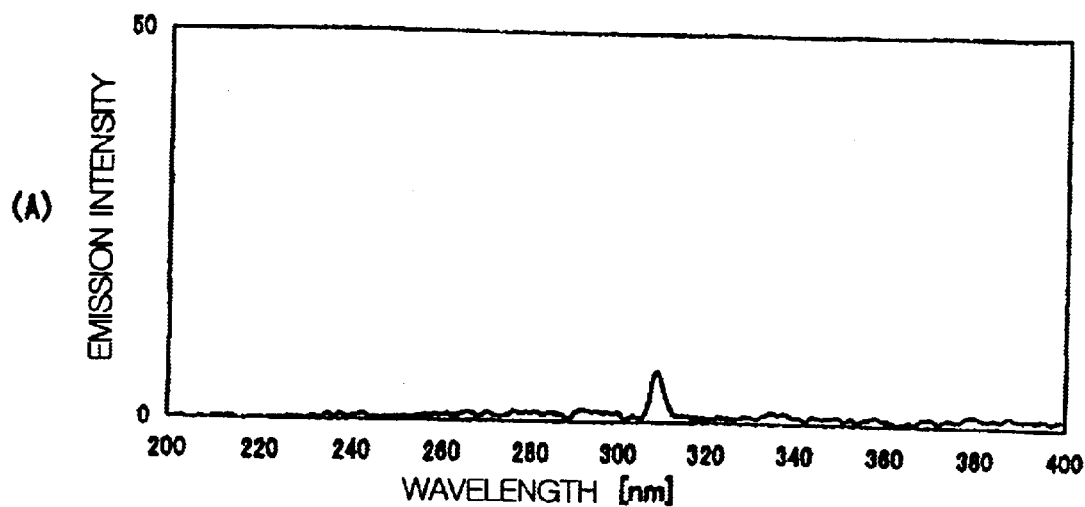
(A)
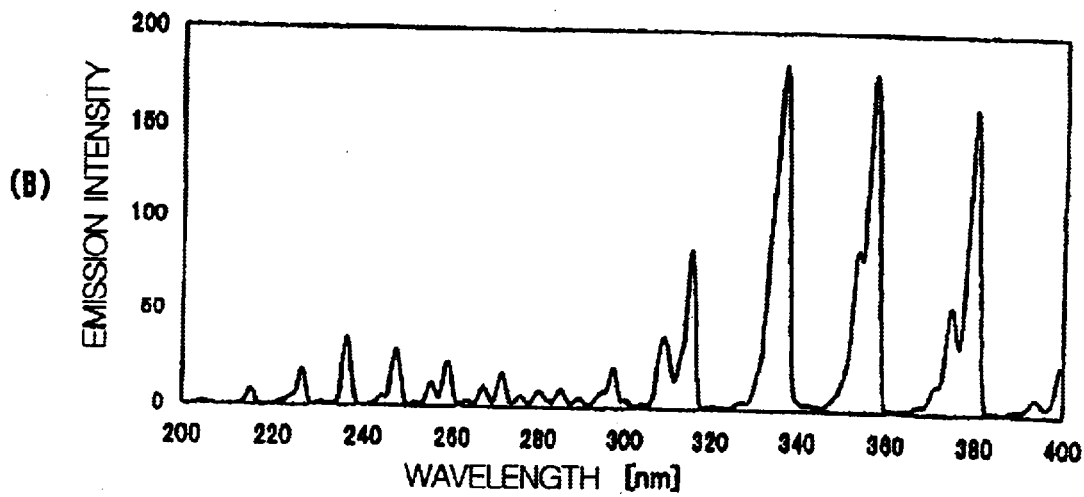
(B)

FIG.4
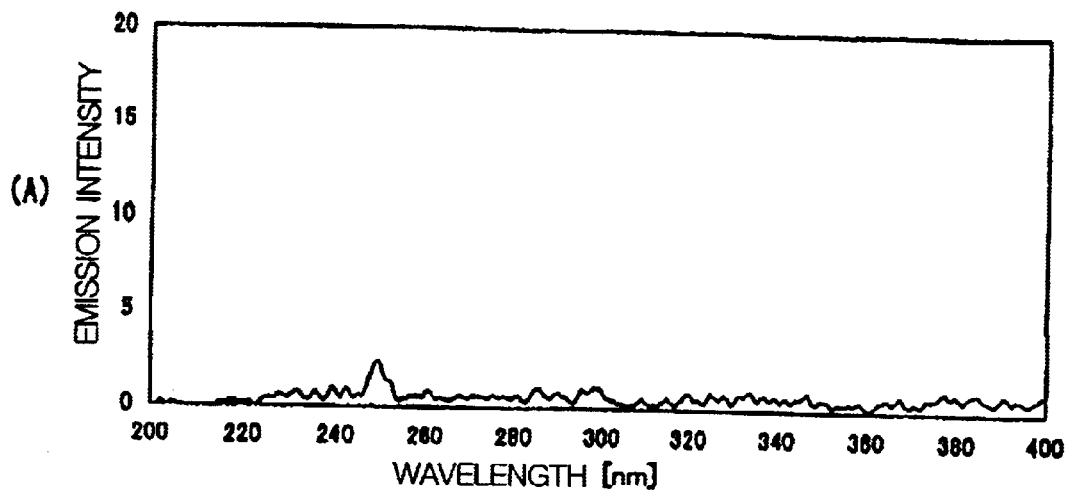
(A)
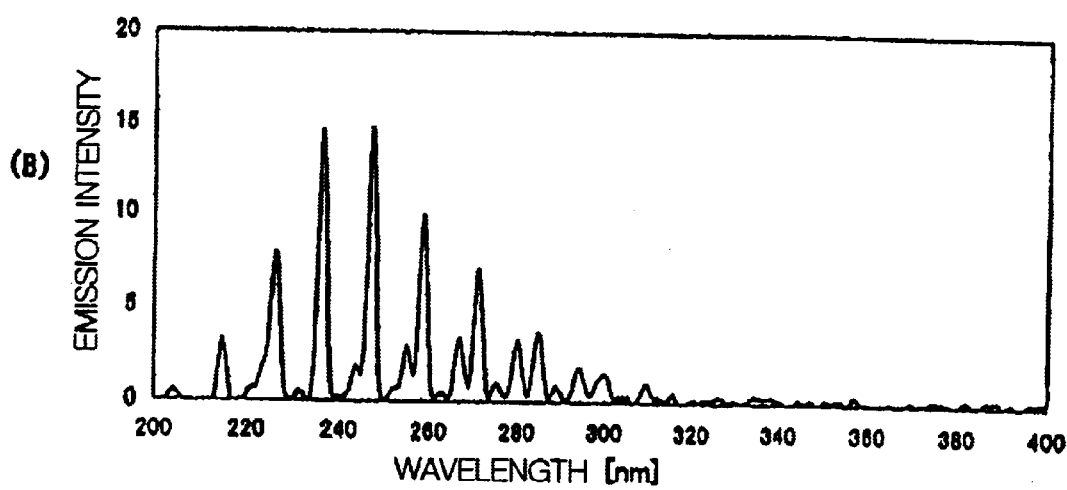
(B)

FIG.10
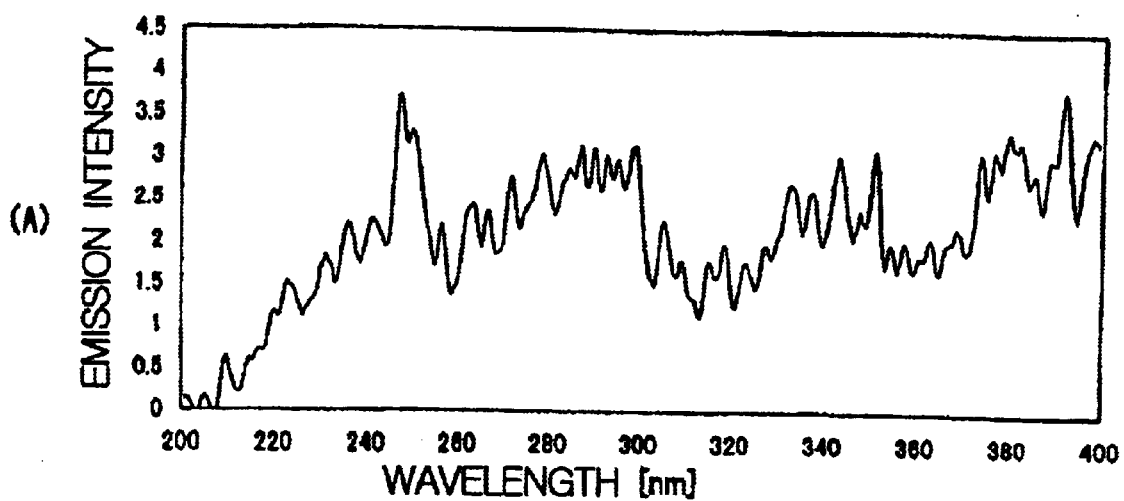
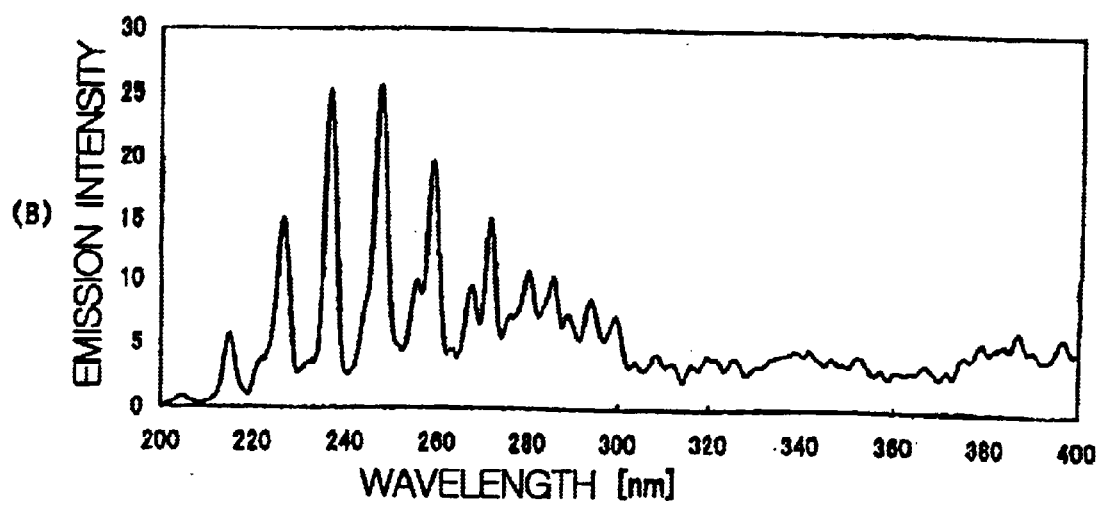

METHOD AND APPARATUS FOR MEASURING NITROGEN IN A GAS

BACKGROUND OF THE INVENTION

1. Field of the Invention

This invention relates to a method and an apparatus for measuring nitrogen in a gas, specifically a method and an apparatus for continuously measuring trace amount of nitrogen in krypton gas or xenon gas.

2. Description of the Prior Art

For example, krypton gas or xenon gas is used in various fields such as the semiconductor manufacturing field or electric device manufacturing field. In particular, in the semiconductor manufacturing field, it has been required to supply a rare gas with a high purity level for a large scale of IC manufacturing.

Purity of gas has a great effect on the product yield of the semiconductor manufacturing process, and thus, is needed to be continuously monitored.

Among the impurities existing in rare gases, nitrogen is used to purge the piping and thus is mixed into the rare gases as an impurity. Moreover, nitrogen is known to decrease the removal ability of a purifier, since it is inactive. Thus, nitrogen is extremely difficult to be removed by a purifier.

In particular, since krypton gas and xenon gas are very expensive, it is getting more and more required that in the analysis process, gas be consumed only in a small amount, and the concentration of trace amounts of nitrogen present in the gas be continuously monitored in real time.

Previously, the trace amounts of nitrogen in krypton gas or xenon gas were measured by GC-MS (gas chromatography-mass spectrometer), which is expensive and can measure only at time intervals. This is a disadvantage, in that, nitrogen concentration cannot be monitored continuously in real time.

Similarly, GC-TCD (thermal conductivity detector-gas chromatography) and GC-PID (photoionization detector-gas chromatography) were used to analyze trace amounts of nitrogen, but they also carry out measurements only at time intervals, and thus is not suitable for monitoring continuously in real time.

Moreover, both analyzers are disadvantageous because the sample gas and carrier gas to be used for GC (gas chromatography) are mixed with each other and thus gas is wasted after measurement. If the sample gas to be measured is a rare gas, such as krypton gas or xenon gas, which is very expensive, running costs increases. And even if the gas is recycled, the purification costs in separating the sample gas from the other gases increases.

As a method for analyzing nitrogen in a gas under atmospheric pressure without using GC, an optical emission analysis method using a glow discharge has been known.

In the above method, discharge is carried out by supplying DC voltage into a discharge tube with a pair of metal electrodes consisting of an anode and cathode, while supplying a sample gas between the electrodes, so that the generated emission of nitrogen is spectrally separated and detected.

However, the glow discharge has inherent disadvantages because a gas cation can collide with the cathode and emit secondary electrons and at the same time decompose the surface of the cathode and emit metal particles; the emitted particles may contaminate the gas, deteriorate the electrodes and cause unstable emission.

In order to solve such problems, a simplified nitrogen analyzer using silent electric discharge, in which metal electrodes are coated with insulating materials, such as glass, and the like, so that the gas and the metal electrodes may not contact each other.

The analyzer supplies high AC voltage to the electrodes enough to maintain a discharge under atmospheric pressure. A sample gas is supplied in a discharge tube at a constant flow rate and is excited by absorbing energy by electron collision or the like. If an energy transition of a gas molecule from high level to low level occurs, an emission of radiant energy, that is, luminescence happens.

As the emission wavelength is specific to the excited gas component, the nitrogen concentration in a gas can be measured by exclusively extracting an emission wavelength of nitrogen using an interference filter and then detecting the intensity thereof.

In particular, the concentration of nitrogen in argon gas, which is used for the above simplified nitrogen analyzer, is measured by separating a wavelength of 337±5 nm or 357±5 nm by using an interference filter and converting the light into an electric signal.

However, as described in the Japanese Patent laid-open Publication Hei 11-326219, since such a simplified nitrogen analyzer needs to use a base gas having a higher ionization potential compared to a gas to be analyzed, it is difficult to measure the nitrogen concentration in krypton gas or xenon gas. And thus, only nitrogen in a rare gas such as argon or helium can be measured.

Therefore, in order to measure the nitrogen concentration in krypton gas or xenon gas using the previous simplified nitrogen analyzer, a GC needs to be installed in the front end part of the analyzer so that the nitrogen in krypton gas or xenon gas is transformed into the nitrogen in argon gas or helium gas. This causes problems in that nitrogen concentration cannot be measured in real time and apparatus costs are increased.

In addition, in the case of measuring concentration of nitrogen in a sample gas using the previous simplified nitrogen analyzer, if an impurity such as oxygen or moisture is contained in the sample gas, nitrogen concentration cannot be accurately measured due to the coexistence effect. Therefore, it is recommended that a purifier for removing the impurity is installed in the sample introduction tube of the analyzer. However, in such a case, the purifier must be replaced before it becomes out of order.

SUMMARY OF THE INVENTION

Under such circumstance, the present invention aims to provide a method and an apparatus for analyzing nitrogen in gas, by which nitrogen concentration can be continuously measured with high accuracy and sensitivity without using GC(gas chromatography) and wasting a sample gas, a purifier for avoiding coexistence effect is not required, generation of coexistence effect or plasma abnormality can be determined without damaging the continuously driving condition of an analyzer, and the presence of unknown impurities can be detected.

In order to obtain the above object, the present claim provides a method for measuring nitrogen in a gas, comprising the steps of:

introducing a sample gas into a discharge tube, collecting an emission light generated by discharge, extracting a wavelength from the light specific to nitrogen, introducing said wavelength to a detector, and continuously measuring the concentration of said nitrogen present in said gas according to the intensity of said light detected by said detector, wherein, at least one of said wavelengths for measuring the nitrogen concentration is selected from a group consisting of 215±2 nm, 226±2 nm, 238±2 nm, 242±2 nm, 246±1 nm, 256±2 nm, 260±2 nm, 266±2 nm, 271±1 nm, 276±4 nm, 285±2 nm, 294±1 nm, and 300±2 nm.

In addition, the present invention provides the method for measuring nitrogen in a gas, further comprising the steps of:

initially measuring an emission intensity of a gas without any impurities, the impurities being capable of creating a coexistence effect on the nitrogen measurement, as a standard emission intensity.

comparing the measured emission intensity of said sample gas with said standard emission intensity, and in case said measured emission intensity is smaller than said standard emission intensity beyond a certain extent, determining whether it results from a disorder of the discharge or presence of an impurity or impurities creating a negative coexistence effect.

The present invention further provides an apparatus for measuring nitrogen in a gas for introducing a sample gas into a discharge tube, collecting an emission light generated by discharge, extracting a wavelength specific to nitrogen from the light, introducing said wavelength to a detector, and continuously measuring the concentration of said nitrogen present in said gas according to the intensity of said light detected by said detector, wherein an interference filter or a spectroscope, which transmits at least one wavelength selected from a group consisting of 215±2 nm, 226±2 nm, 238±2 nm, 242±2 nm, 246±1 nm, 256±2 nm, 260±2 nm, 266±2 nm, 271±1 nm, 276±4 nm, 285±2 nm, 294±1 nm, and 300±2 nm, is installed in front of the detector.

The present invention further provides the apparatus for measuring nitrogen in a gas, further comprising:

means for initially measuring an emission intensity of a gas which does not include any impurities, the impurities being capable of creating a coexistence effect on nitrogen measuring, as a standard emission intensity;

means for comparing the measured emission intensity of said sample gas with said standard emission intensity; and in case said measured emission intensity is smaller than said standard emission intensity beyond a certain extent, means for determining whether it results from a disorder of the discharge or presence of an impurity or impurities creating a negative coexistence effect.

In particular, the present invention further provides an apparatus and a method for measuring nitrogen in a gas, wherein the sample gas is rare gas and selected from a group consisting of:

krypton gas;

xenon gas;

a mixture of krypton gas and xenon gas;

a mixture of krypton gas and at least argon gas, helium gas and/or neon gas;

a mixture of xenon gas and at least argon, helium and/or neon;

a mixture of xenon gas, krypton gas and at least argon, helium and/or neon.

BRIEF DESCRIPTION OF THE DRAWINGS

For a fuller understanding of the nature and objects of the present invention, references should be made to the following detailed description taken in conjunction with the accompanying drawings in which:

FIG. 3 depicts an emission spectrum showing the influence of the presence of nitrogen in argon gas, according to Reference Example 1.

FIG. 4 depicts an emission spectrum showing the influence of the presence of nitrogen in krypton gas according to Reference Example 2.

FIG. 10 is an emission spectrum showing the influence of the presence of nitrogen in a mixture of krypton gas and argon gas according to Reference Example 3.

DETAILED DESCRIPTION OF THE PREFERRED EMBODIMENTS

Figure 2:
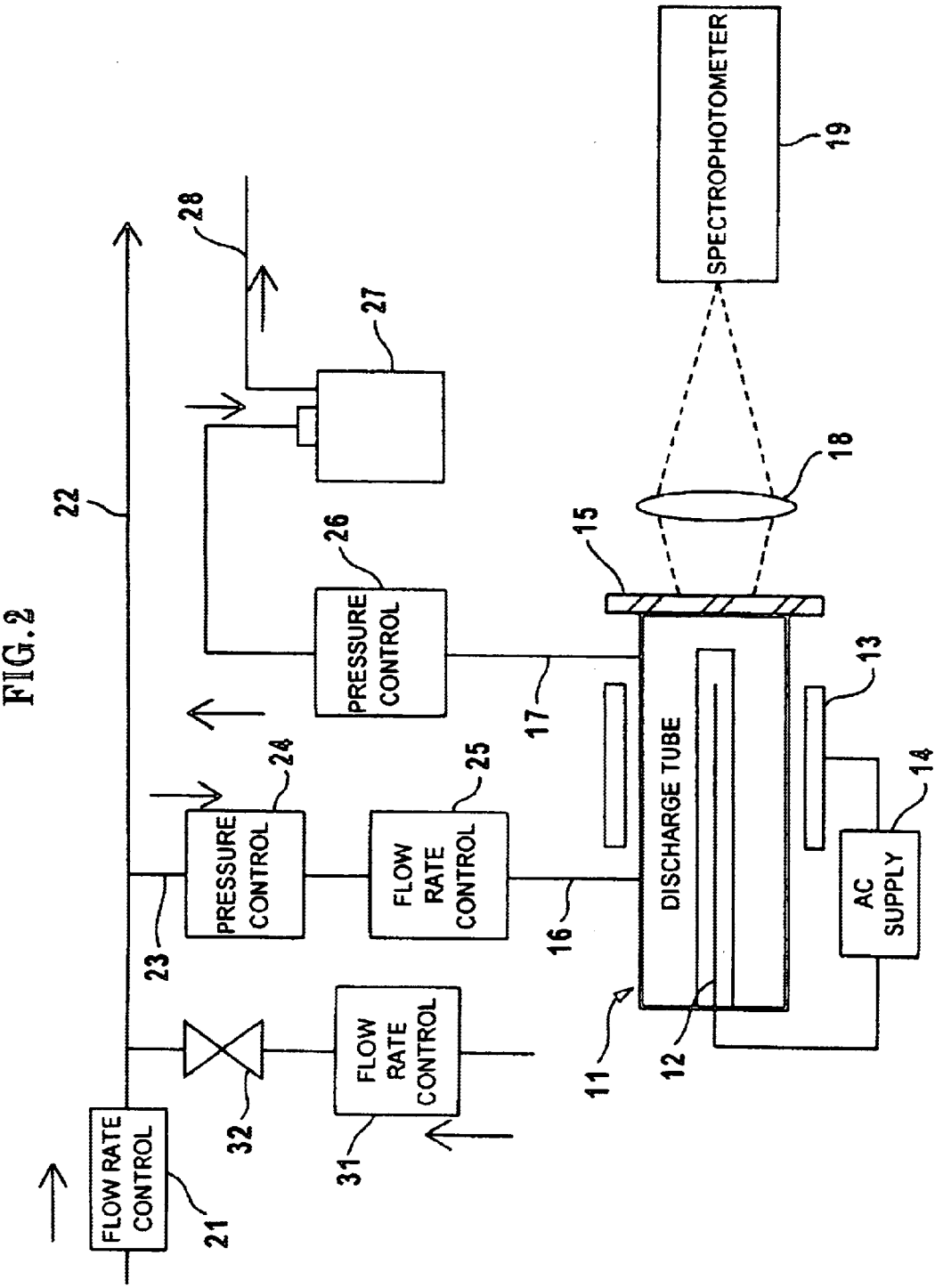
FIG. 2 is a system diagram showing an embodiment of an analyzer using a discharge tube, internal electrodes of which are coated with glass.

First, FIG. 2 is a systematic diagram showing an embodiment of an analyzer using a discharge tube, internal electrodes of which are coated with glass, and which is provided to examine the difference of nitrogen emission spectra between nitrogen in argon gas and nitrogen in krypton gas.

A discharge tube 11 of the analyzer is provided with internal electrodes 12 coated by glass or the like therein and outer electrodes 13 mounted outside of each of the internal electrodes 12, which are connected to a high voltage power supply 14 for AC voltage. One end of the tube 11 is provided with a quartz window 15 and both ends of the tube 11 are provided with a sample gas introduction route 16 and a sample gas releasing route 17, respectively.

A sample gas to be analyzed is supplied to a main line 22 from a flow rate control device 21.

From the main line 22, an analysis line 23 branches off toward the discharge tube 11 to allow a part of the sample to flow toward said discharge tube 11 via a pressure control device 24, a flow rate control device 25 and the sample gas introduction route 16, at a predetermined pressure and flow rate.

The gas released from the discharge tube 11 into the sample gas releasing route 17 is drained via a pressure control device 26, a tank 27 and a line 28.

The light generated by the discharge in the discharge tube 11 is collected by a lens 18 via the quartz window 15 and the intensity thereof is measured by a spectrophotometer 19.

In the above analyzer in which argon gas or krypton gas were set as the gases supplied from the flow rate control device 21, argon gas or krypton gas containing nitrogen gas were introduced from a flow rate controller 31 for added gas via a valve 32, emission spectra were measured for the respective argon gas or krypton gas, each of which contains nitrogen.

In the result, in the case of argon gas, as shown in FIG. 3(A) (not containing nitrogen) and FIG. 3(B) (containing nitrogen), there is a big signal around 337 nm when nitrogen exists, while in the case of krypton gas, as shown in FIG. 4(A) (not containing nitrogen) and FIG. 4(B) (containing nitrogen), there is no signal around 337 nm even when nitrogen exists.

Therefore, in the case of krypton gas containing nitrogen, it is apparent from FIG. 4(B) that signals with peak wavelengths of 215±2 nm, 226±2 nm, 238±2 nm, 242±2 nm, 246±1 nm, 256±2 nm, 260±2 nm, 266±2 nm, 271±1 nm, 276±4 nm, 285±2 nm, 294±1 nm and 300±2 nm are obtained.

Figure 1:
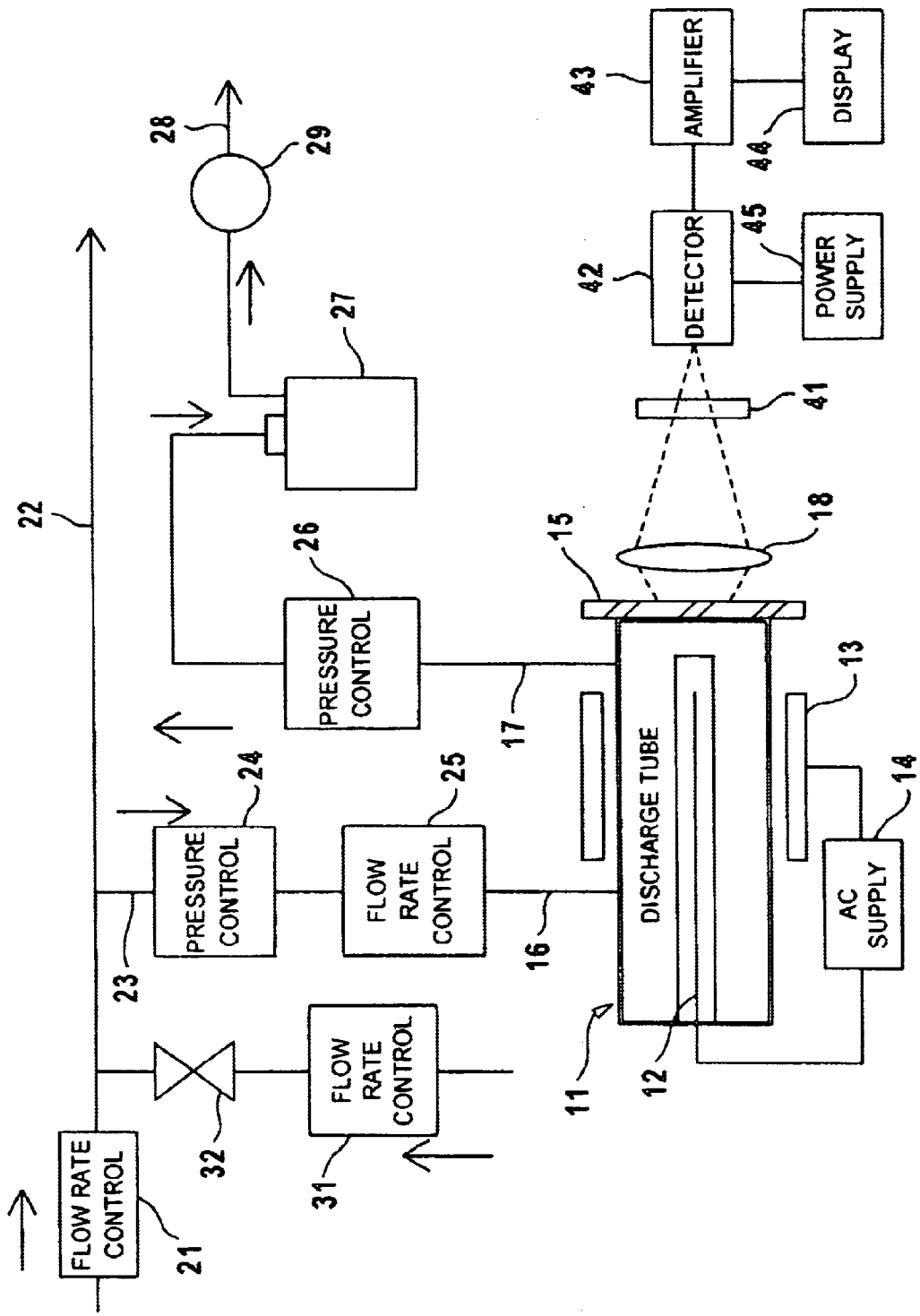
FIG. 1 is a system diagram showing the 1st embodiment of an apparatus according to the present invention.

FIG. 1 is a systematic diagram showing an embodiment of the present invention. In the following, the same constitutional elements as in FIG. 2 are explained by the same reference numbers, without detailed explanation.

In this nitrogen measuring apparatus, a sample gas flows to a main line 22 via a flow rate control device 21. A part of the sample gas branches off in an analysis line 23 toward a discharge tube 11 via the main line 22, is introduced into the discharge tube 11 while the pressure and flow rate thereof are controlled by a pressure control device 24 and a flow rate control device 25, and then collected into a tank 27 via a pressure control device 26.

The tank 27 is provided with a boosting means 29, which sends back the collected gas in the tank, from a line 28 to the main line 22 (not shown). Thus, nitrogen as an impurity can be continuously measured while the sample gas is not wasted but reused.

High AC voltage is supplied from a high voltage power supply 14 for discharge to the electrodes 12, 13 installed inside and outside of the discharge tube 11. The light generated from the discharge is collected from a quartz window 15 mounted in the discharge tube 11 via a lens 18. A certain wavelength, which is selected via an interference filter 41, is exclusively introduced into a detector 42 and then converted into an electric signal according to its emission intensity.

This electric signal is signal-amplified by an amplifier 43 and output on a display 44.

In addition, a detector 42 is provided with a high voltage power supply 45 as a driving force.

In addition, when the sample gas collected in the tank 27 is sent back from the line 28 to the main line 22, if the pressure of the main line 22 is lower than the inner pressure of the discharge tube 11, the boosting means 29 in the tank 27 needs not be operated, and the pressure control device 26 can be used as boosting means. The impurity to be measured is not limited to nitrogen. Other impurities such as moisture, methane and the like can be measured at the same time.

The interference filter 41 can selectively transmit an emission wavelength specific to an impurity. In the case of nitrogen, an interference filter for measuring an impurity concentration without affecting the emissions from other gas components in a sample gas has at least one peak wavelength of transmitted light selected from a group consisting of 215±2 nm, 226±2 nm, 233±2 nm, 242±2 nm, 246±1 nm, 256±2 nm, 260±2 nm. 266±2 nm, 271±1 nm, 276±4 nm, 285±2 nm, 294±1 nm and 300±2 nm.

In addition, in the case of measuring moisture simultaneously, it is preferable to use an interference filter to transmit light with a peak wavelength of 308±5 nm or 280±5 nm, while in the case of measuring methane simultaneously, it is preferable to use an interference filter to transmit light with a peak wavelength of 430±5 nm.

To extract only one emission peak, the half width is preferably 1–5 nm, while an interference filter with wider range of 5–30 nm can be used to extract a plurality of emission peaks.

Instead of the interference filter 41, other means such as a monochrometer for extracting a certain wavelength can be used.

If the impurity concentration in a sample gas is too high, the emission intensity measured at the wavelength sometimes becomes so strong such that the detector is saturated and an accurate measurement cannot be obtained.

In such a case, the following options are available decrease the discharge voltage to around 5,000V so as to weaken the emission intensity, lower the amount of the incident light into the detector 42, or carry out the measurement using a wavelength with low sensitivity(for example, 260±2 nm in the case of nitrogen).

Figure 5:
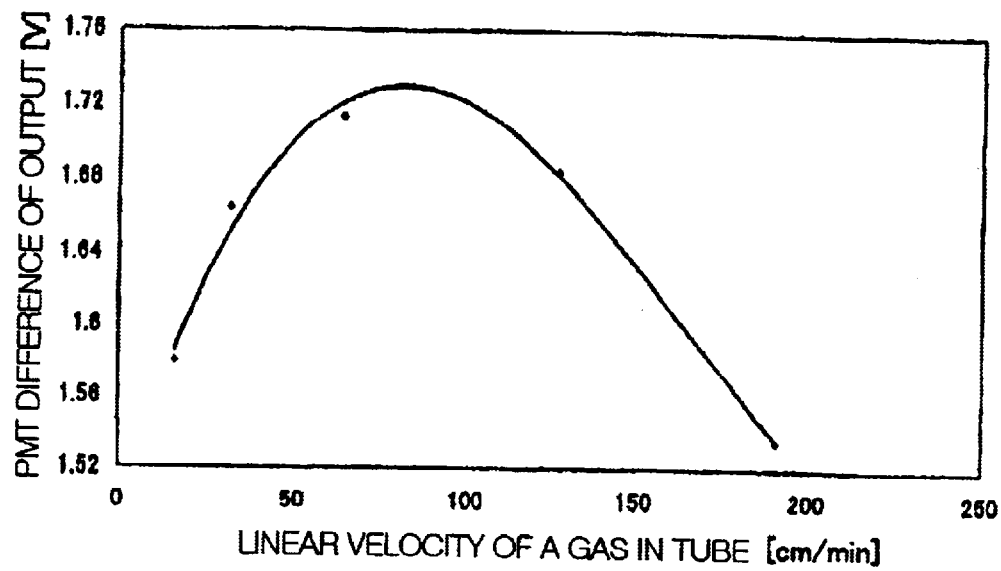
FIG. 5 is a graph showing the relationship between the linear velocity of the sample gas in a discharge tube and the difference of the output of the detector according to Example 1.

The linear velocity of the sample gas introduced into the discharge tube 11 after being regulated to a predetermined flow rate by the flow rate control device 25, is preferably above 0.3 cm/min (25° C., 1 atm). However, as shown in FIG. 5, when the linear velocity is in the range of 60~100 cm/min, the difference of output (PMT difference of output) of the detector 42 become larger, and thus it is advantageous to select the gas flow rate so that the linear velocity may be within the above range.

Figure 6:
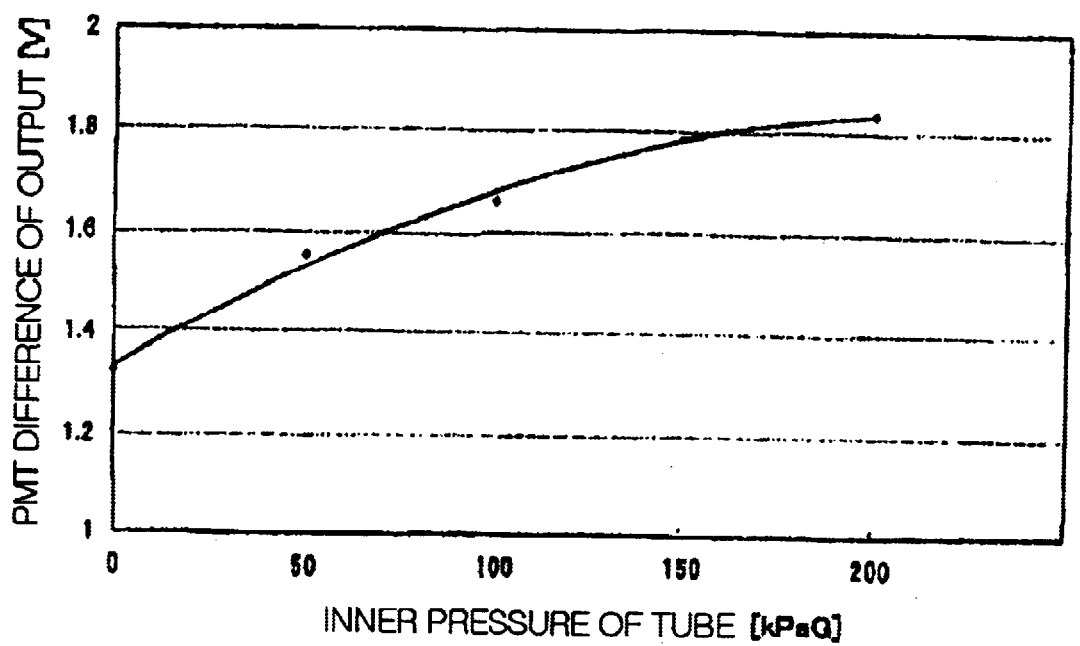
FIG. 6 is a graph showing the relationship between the pressure of the sample gas in a discharge tube and the difference of the output of the detector according to Example 2.

The pressure in the discharge tube 11 may be selected within the range of 1~300 kPaG. As shown in FIG. 6, however, high pressure may increase the difference of output of the detector (PMT difference of output) 42, and thus, it is preferable to set the pressure above atmospheric pressure.

The voltage to be supplied to the electrodes 12, 13, for maintaining the discharge between the electrodes, is preferably AC 10,000V.

The impurity concentration in the sample gas may be obtained by an emission intensity compared to a calibration curve, which is measured at the same condition in advance.

The impurity concentration may be displayed to the displayer 44 which calculates the impurity concentration. A personal computer can be used instead of the displayer 44.

The detector 42 is preferably a photomultiplier tube, but it is also possible to convert a photo signal to an electric signal using photodiode or photodiode array.

Rather than using the detector 42, the high voltage power supply 45 and the amplifier 43, an integration of such units of a detector module may be used.

Further, it is preferable to install a pressure control device 26 into a sample gas releasing route 17 of the discharge tube 11 in order to stabilize the discharge in the discharge tube 11. However, the measurement may be carried out without such an apparatus to save costs and if only a rough measurement is needed.

The base gas of the sample gas in the case of analyzing nitrogen, is not limited to krypton gas and xenon gas, but may be selected from argon, helium, neon or mixtures thereof.

The main object of the present invention by which trace amounts of nitrogen in a gas can be measured, is to continuously monitor the purity of a rare gas with high purity, and the present invention can be applied to control monitor of an apparatus for supplying rare gas with high purity.

Such an apparatus is usually mounted to a semiconductor manufacturing process using various types of gases, and sometimes different types of gases are mixed in the same process.

In such a case, it is preferable for the apparatus to be able to qualitatively detect the mixture of the other components as well as impurity nitrogen.

It is known that a spectroscopic analysis using an atmospheric plasma is easily affected by coexistent materials (coexistence effect).

Likewise, the present invention also shows coexistence effects, such as sensitivity change or baseline change, while the degrees of such effects thereof are different depending on the components.

If such an effect is high, the sensitivity to the analytical object component is decreased significantly. Thus, even if the actual amount of the analytical object component is enough to be easily detected without the coexistence effect, there is a possibility that the component cannot be appropriately detected and the output will show that the component is not contained.

A control monitor of a gas supply apparatus, such an incorrect information report may cause the operation of the supply apparatus to falter.

Therefore, a concentration of a material with coexistence effect may be measured in advance when measuring the nitrogen concentration and then the nitrogen concentration is corrected according to the concentration of the material.

Figure 7:
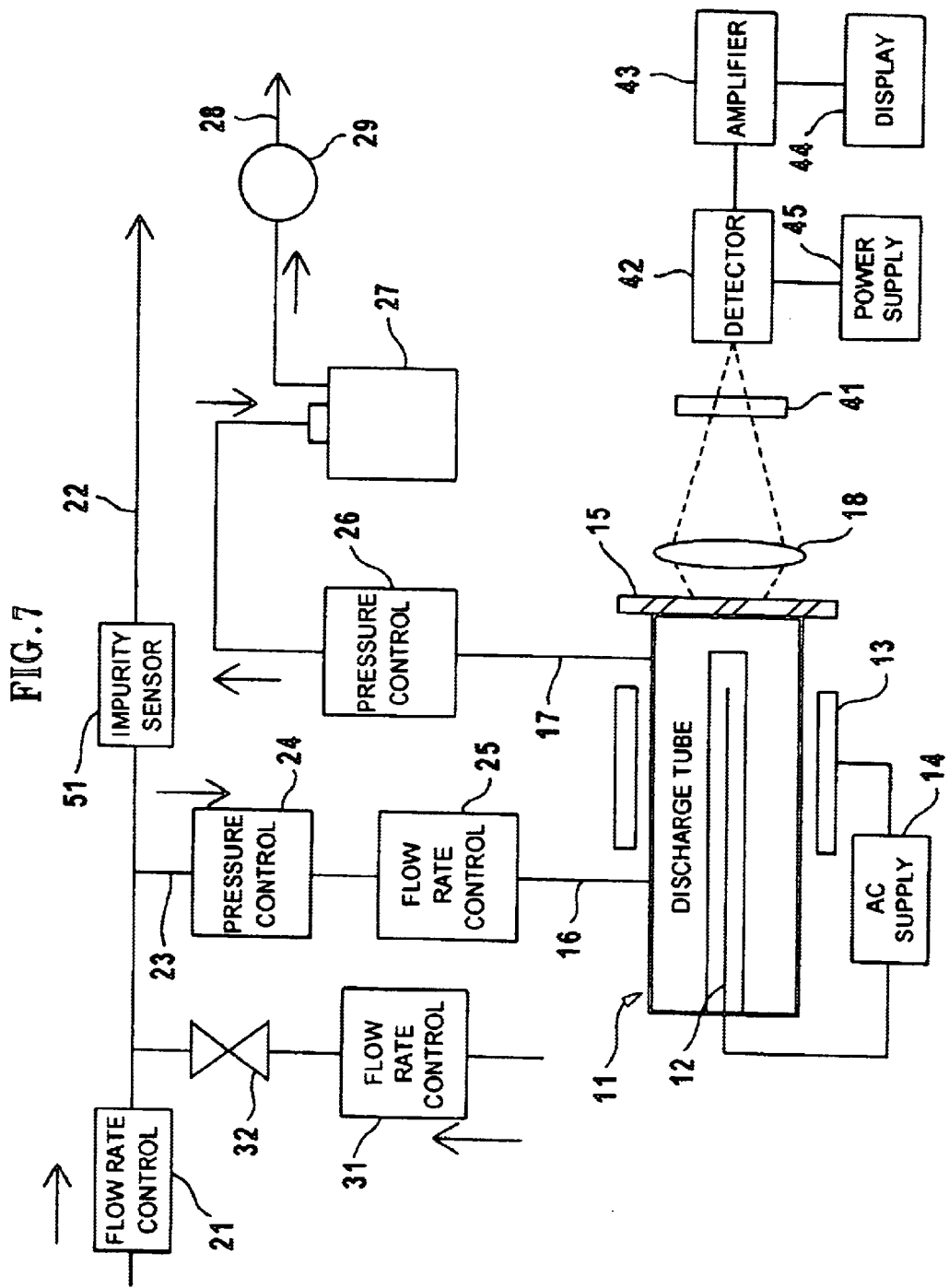
FIG. 7 is a systematic diagram showing an embodiment of an apparatus, taking into consideration the coexistence effect.

FIG. 7 is a systematic diagram showing an embodiment of an analyzer prepared in consideration of a coexistence effect, in which an impurity sensor 51 is installed in the main line 22.

In FIG. 7, the same constitutional elements as in FIG. 1 are explained with the same reference numbers without detailed description.

As for the impurity sensor 51, it is common to use an oxygen sensor, but other sensors capable of detecting materials which are expected to be mixed into the sample gas, such as moisture, argon and helium, may be used.

The analyzer corrects a nitrogen concentration by receiving an impurity concentration signal from the impurity sensor 51, and produces a correct nitrogen concentration even when the amount of impurity is changed.

However, in such an analyzer, which operates while sending or receiving signals to or from a plurality of analyzers or sensors, the management of the process may become complicated and costly, depending the an analytical object, for example in the case of using a single gas.

On the other hand, the present inventors found that the base line changes under such coexistence effect, and that using such a phenomenon, the presence of the other components coexist can be detected, that is, whether the other components are mixed.

For example, if argon or helium co-exists in a sample gas, the base line of nitrogen emission in krypton gas tends to increase.

Since such an increase is often caused by the actual increase of nitrogen concentration, it is difficult to detect whether a component capable of raising a base line is mixed.

However, oxygen lowers the intensity of a base line, and moisture also shows such a result, although the degree varies depending on the kind of matrix gases.

Therefore, if the base line is lowered, it can be regarded that there is a disorder in the analyzer or the measurement.

Oxygen or moisture is a main component of air, and thus can easily be mixed into the sample gas due to external leakage of gas piping or disorder of gas separation process. Therefore, it is advantageous to be able to detect such impurities.

As shown above, by monitoring the decrease of the base line, whether impurity components exist can be detected. Further, since such a decrease of base line can be found even when discharge is stopped due to the problems that can occur, the abnormality can be properly detected.

For example, in calibrating an analyzer, a high-purity gas in which the object component to be measured and components with coexistence effect are sufficiently low, is subject to passing through the analyzer. The emission intensity (base level) is then measured and memorized as a standard emission intensity.

Then, the emission intensity measured by subjecting the sample gas through the analyzer, that is, the measured emission intensity is compared with the above standard emission intensity. If the measured emission intensity is lower than the standard emission intensity beyond a certain extent, it is judged whether such deviation results from disorder of the apparatus such as discharge interruption or mixture of impurities with a coexistence effect, and it is informed the operator by alarm and the like.

The means for memorizing the standard emission intensity, the means for comparing the measured emission intensity and the standard emission intensity and means for carrying out a judgment based on the compared results, can be provided by designing an apparatus with a memory computing element. For example, a memory computing apparatus which has been previously installed for control and measurement of the analyzer or a commercial personal computer can be used.

A data abnormality is determined, for example, by obtaining the reproducibility of the standard emission intensity, setting three times the variation range thereof as a threshold value, and if the measured emission intensity goes below the threshold value, judging it abnormal. The threshold value, however, can be pertinently selected depending on the characteristic of the process to be monitored.

Embodiments

REFERENCE EXAMPLE 1

With respect to the apparatus shown in FIG. 2, in which argon gas was supplied from the flow rate control device 21 and argon gas containing nitrogen was supplied from the flow control device 31, the valve 32 was switched so that the argon gas without nitrogen and the argon gas containing nitrogen were introduced one after the other into the discharge tube 11, and then the emission spectra generated by the discharge were measured by the spectrophotometer 19.

The discharge voltage was AC 10,000V, the pressure in the discharge tube was atmospheric pressure, the total flow rate of the gas supplied to the discharge tube was 50 cc/min, and the nitrogen concentration in the argon gas was 0.44%.

The obtained spectra are shown in FIG. 3(A), (B). It can be found from the spectrum of FIG. 3(B) that the nitrogen in the argon gas has a strong emission signal around 337 or 357 nm.

REFERENCE EXAMPLE 2

With respect to the apparatus shown in FIG. 2, in which krypton gas was supplied from the flow rate control device 21 and krypton gas containing nitrogen was supplied from the flow control device 31, the valve 32 was switched so that the krypton gas without nitrogen and the krypton gas containing nitrogen were introduced one after the other into the discharge tube 11, and then the emission spectra generated by the discharge were measured by the spectrophotometer 19.

The measurement conditions for reference example 2 were identical with those of the reference example 1, except for the type of gas used.

The obtained spectra are shown in FIG. 4(A), (B). It can be found from the FIG. 4(B) that the nitrogen in the krypton gas has strong emission signals at around 238 nm and 248 nm (not around 337 and 357 nm).

EXAMPLE 1

With respect to the apparatus shown in FIG. 1, krypton gas was supplied from the flow rate control apparatus 21 and krypton gas containing nitrogen was supplied from the flow rate control apparatus 31, and the nitrogen concentration was regulated to a desired concentration by the flow rate apparatus 31.

The krypton gas containing a determined concentration of nitrogen and the krypton gas without nitrogen were respectively supplied to the discharge tube 11, and the respective emission intensities thereof were measured while varying the total gas flow rate in the range of 15–200 cm/min.

Figure 8:
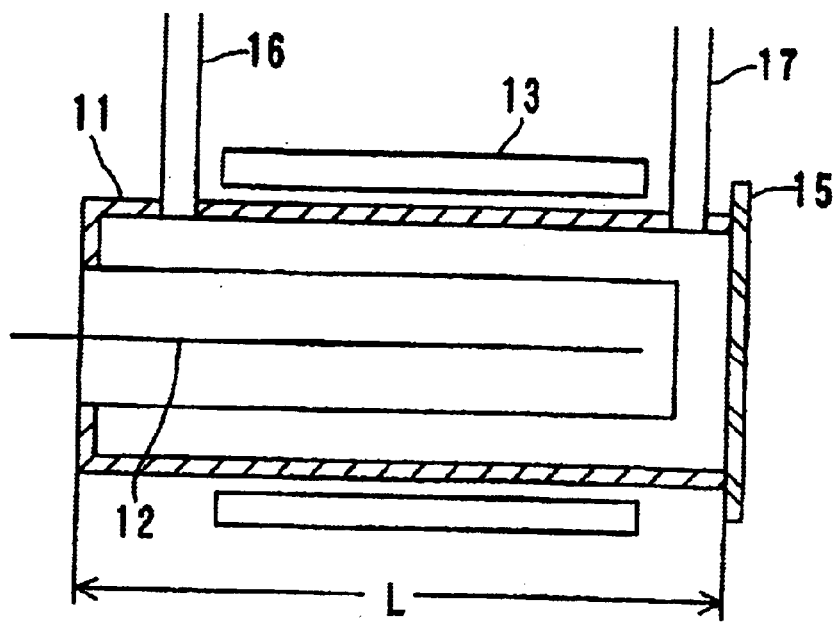
FIG. 8 is a front sectional view showing a discharge tube used in Example 1.
Figure 9:
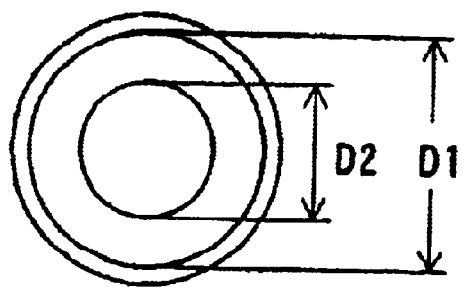
FIG. 9 is a side sectional view showing a discharge tube used in Example 1.

As shown in FIGS. 8 and 9, the discharge tube had a discharge tube length L of 230 mm, an inner diameter D1 (the discharge tube 11) of 25 mm, an outer diameter D2 (the internal electrode 12) of 15 mm, and a cross section of the flow passage of 314 mm$^2$.

The measurement conditions were as follows.
discharge voltage: AC 10,000V; internal pressure of the discharge tube: 50 kPaG; nitrogen concentration in krypton gas: 0 ppm and 10 ppm; measurement wavelength: 238 nm.

FIG. 5 shows the change of the emission intensity to the linear velocity. This result shows that the emission intensity of nitrogen increases according to the increase of the linear velocity initially, but has a tendency to decrease when the linear velocity exceeds 80 cm/min. The preferable flow rate condition is 60–100 cc/min of linear velocity.

EXAMPLE 2

The emission intensity was measured when the gas flow rate of the discharge tube was 50 cc/min and the inner pressure of the discharge tube was varied within the range of 0–200 kPaG.

The other conditions were identical to those of Example 1. The result showed that as the pressure is increased, the sensitivity is improved as shown in FIG. 6.

REFERENCE EXAMPLE 3

With the apparatus shown in FIG. 2, in which a mixed gas of krypton gas and argon gas was supplied from the flow rate control device 21 and nitrogen was supplied from the flow control device 31, the valve 32 was switched so that the mixed gas of krypton gas and argon gas without nitrogen and the mixed gas of krypton gas and argon gas containing nitrogen were introduced one after the other into the discharge tube 11, and then the respective emission spectra generated by discharge were measured by the spectrophotometer 19. The measured results are shown in FIG. 10(A) and (B).

The measurement conditions were as follows.
discharge voltage: AC 10,000V; inner pressure of the discharge tube; atmospheric pressure; total gas flow rate: 50 cc/min; argon gas concentration in krypton gas; 20%; nitrogen gas concentration in the mixed gas of krypton gas and argon gas; 236 ppm.

FIG. 10(A) of the case without nitrogen and FIG. 10(B) of the case with nitrogen show that the emission of nitrogen in the mixed gas of krypton gas and argon gas was different from that of the nitrogen in argon gas. No emission signal was obtained at around 337 nm or 357 nm but strong signals were obtained at around 238 nm and 248 nm.

EXAMPLE 3

With respect to the apparatus shown in FIG. 1, krypton gases of 6 different nitrogen contents (0 ppm, 11.1 ppm, 21.8 ppm, 32.0 ppm, 51.5 ppm, 69.5 ppm) were introduced one after another into the discharge tube 11 by switching the gases at 15 minutes intervals.

The measurement conditions were as follows.
discharge voltage: AC 10,000V; inner pressure of the discharge tube; atmospheric pressure; total gas flow rate: 49.5 cc/min; measurement wavelength: 238 nm.

Figure 11:
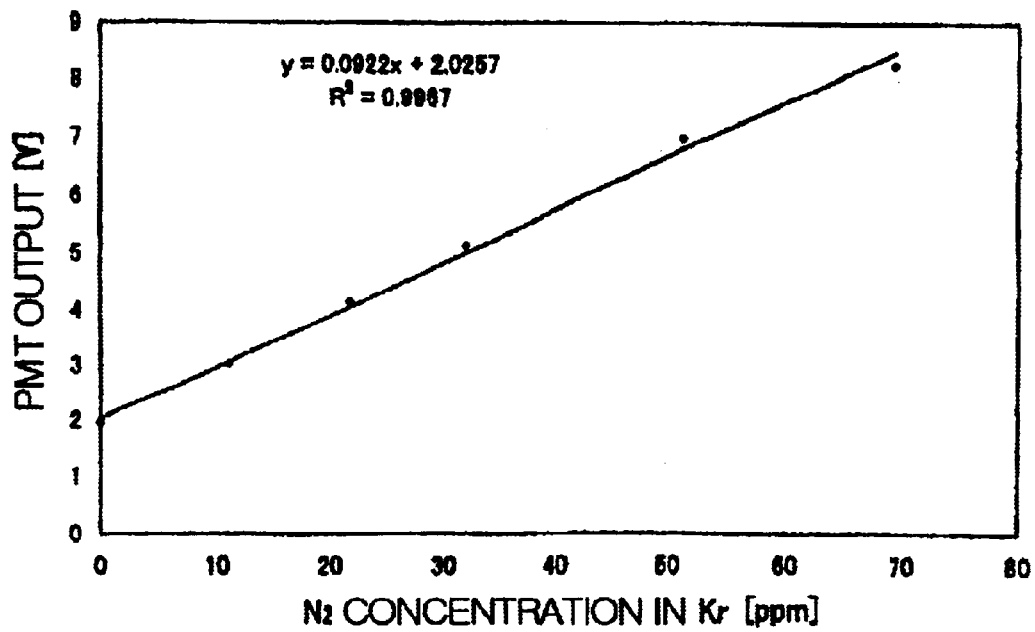
FIG. 11 is a graph showing a relationship between the nitrogen concentration in krypton gas and emission intensity according to Example 3.
Figure 12:
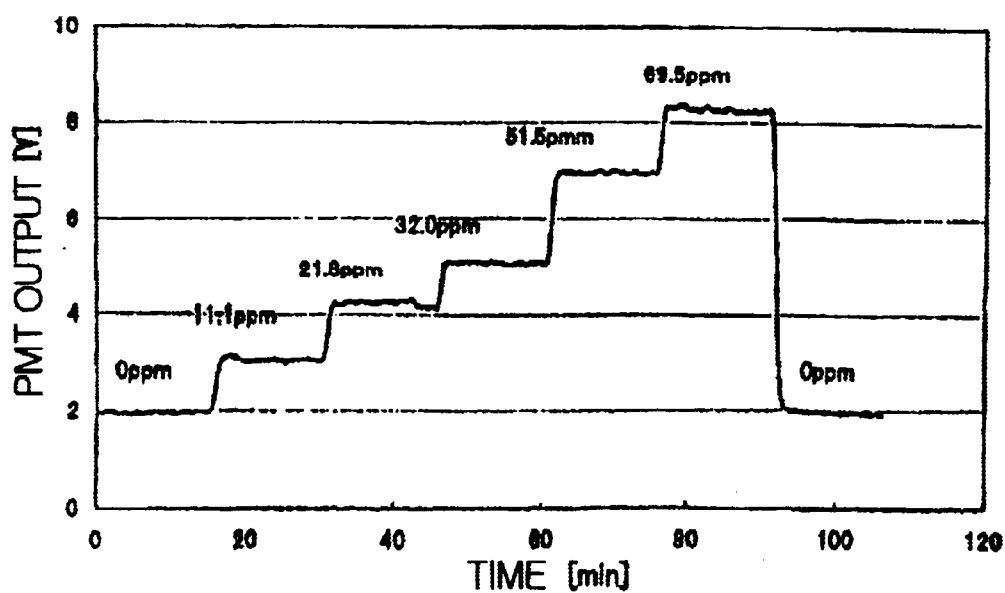
FIG. 12 is a graph showing an emission intensity as a function of time according to Example 3.

The relation of the emission intensity to the nitrogen concentration is shown in FIG. 11, and the relation of the emission intensity to time is shown in FIG. 12.

The result shows that the nitrogen concentration is linearly proportional to the emission intensity.

EXAMPLE 4

With respect to the apparatus shown in FIG. 1, xenon gases of 3 different nitrogen contents (0 ppm, 298 ppm, 596 ppm) were respectively introduced into the discharge tube 11 and the correspondent 3 emission intensities were measured.

The measurement conditions were as follows.
discharge voltage: AC 10,000V; inner pressure of the discharge tube; atmospheric pressure; total gas flow rate: 47.6 cc/min; measurement wavelength: 246 nm.

Figure 13:
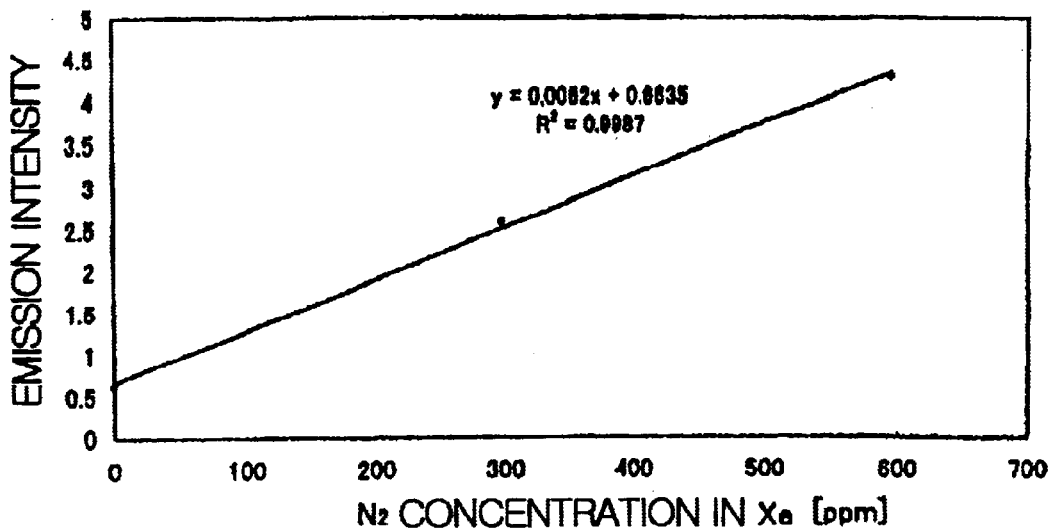
FIG. 13 is a graph showing a relationship between the nitrogen concentration and emission intensity according to Example 4.

The relation between the obtained emission intensity and the nitrogen concentration is shown in FIG. 13. The result shows that the nitrogen concentration is linearly proportional to the emission intensity.

EXAMPLE 5

With respect to the apparatus shown in FIG. 1, argon gases of 6 different nitrogen contents (0 ppm, 2 ppm, 4 ppm, 6 ppm, 8 ppm, 10 ppm) were respectively discharged and the 6 correspondent emission intensities of nitrogen were measured.

The measurement conditions were as follows.
discharge voltage: AC 10,000V; inner pressure of the discharge tube: atmospheric pressure; total gas flow rate: 48 cc/min; measurement wavelength: 238 nm.

Figure 14:
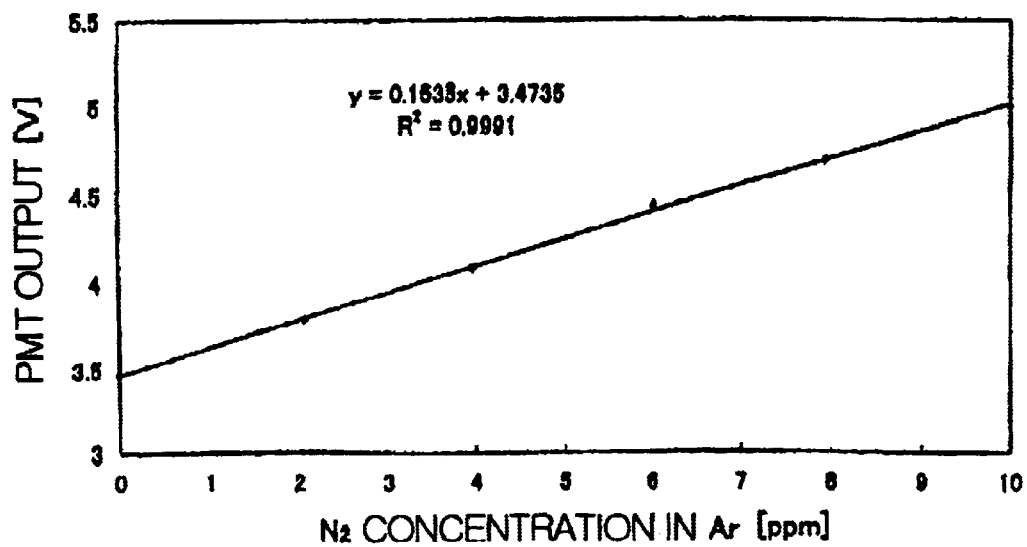
FIG. 14 is a graph showing a relationship between the nitrogen concentration and emission intensity according to Example 5.

The relation between the obtained emission intensity and the nitrogen concentration is shown in FIG. 14.

The result shows that the nitrogen concentration is linearly proportional to the emission intensity.

EXAMPLE 6

With respect to the apparatus shown in FIG. 1, in which krypton gas was supplied from the flow rate control device 21 and argon gas was supplied from the flow control device 31, the argon gas concentration was changed by regulating the flow control device 31 and the change in the emission intensity according to the argon gas concentration was measured.

The measurement conditions were as follows.
discharge voltage: AC 10,000V; inner pressure of the discharge tube: atmospheric pressure; total gas flow rate: 47.9 cc/min; argon gas concentration: 0–100%; measurement wavelength; 238 nm.

Figure 15:
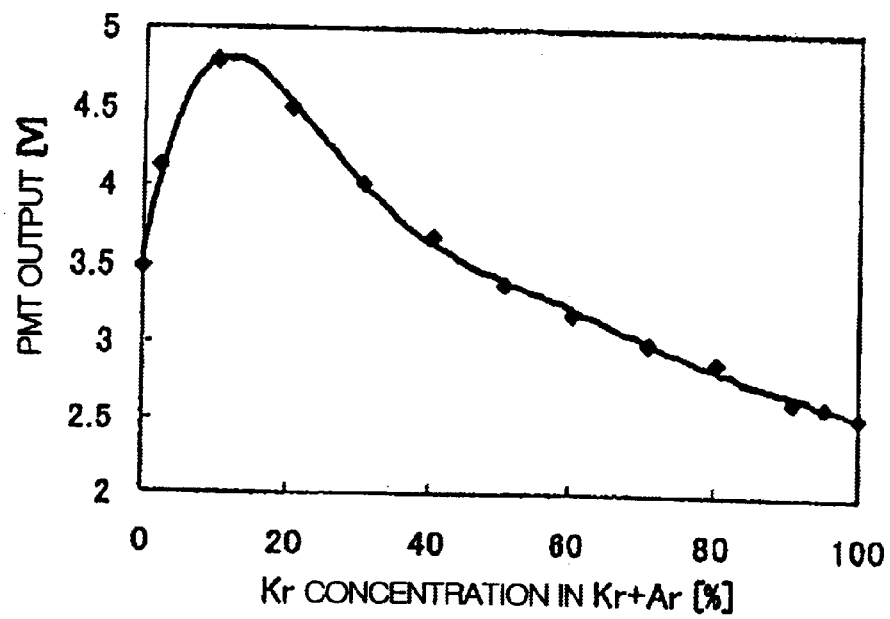
FIG. 15 is a graph showing a relationship between the argon gas concentration in krypton gas and emission intensity according to Example 6.

The measured results are shown in FIG. 15.

The result shows that if argon gas is mixed into the krypton gas, the base line increases compared to when only krypton gas is discharged, and thereby the mixture of argon (impurity) can be detected.

The same result was obtained when helium gas was used instead of argon gas.

EXAMPLE 7

With respect to the apparatus shown in FIG. 1, in which krypton gas was supplied from the flow rate control device 21 and oxygen gas was supplied from the flow control device 31, the valve 32 was switched so that the krypton gas containing oxygen and krypton gas without oxygen gas may flow into the discharge tube 11 alternatively, and then the respective emission intensities were measured. All the conditions except for the kinds and concentrations of the gas were identical to those of Example 6.

Figure 16:
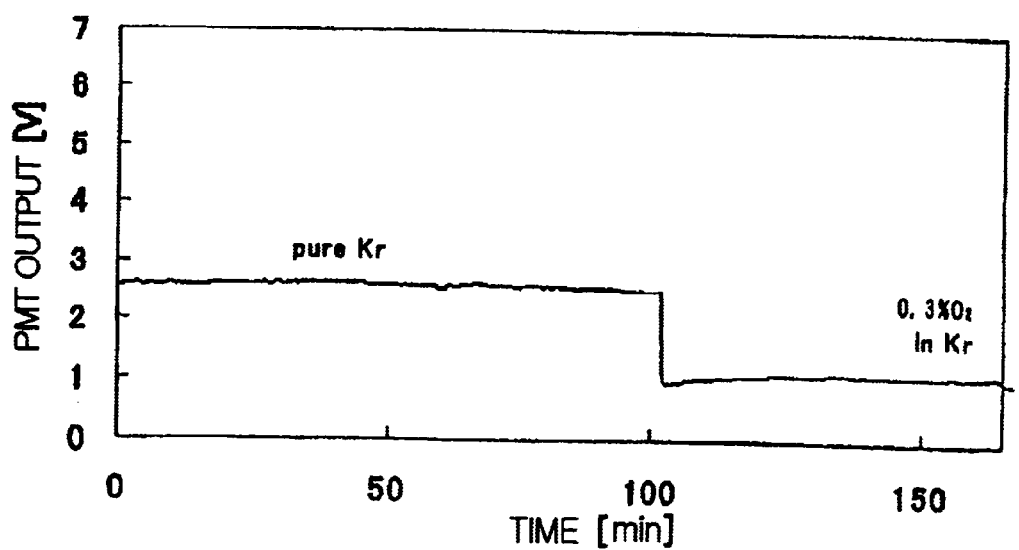
FIG. 16 is a graph showing the change of emission intensity when oxygen is added into the krypton gas according to Example 7.

The measured results are shown in FIG. 16.

The result shows that if oxygen is mixed into krypton gas, the base line decreases compared to when only krypton gas is discharged, and thereby the mixture of oxygen (impurity) can be detected.

EXAMPLE 8

With respect to the apparatus shown in FIG. 7, in which pure krypton gas and krypton gas containing 28 ppm of nitrogen were supplied from the flow rate control device 21 and oxygen gas was supplied from the flow control device 31, the flow control device 31 was regulated so that the oxygen concentration in the pure krypton gas and the krypton gas containing 28 ppm of nitrogen may be predetermined values (0 ppm, 20 ppm, 40 ppm, 60 ppm, 80 ppm), and the respective correspondent emission intensities were measured.

Figure 17:
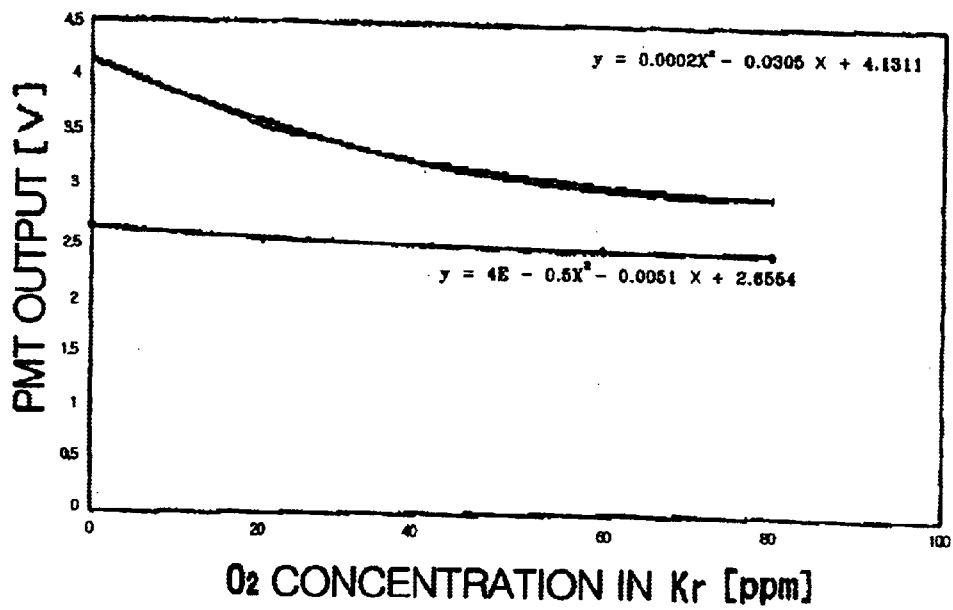
FIG. 17 is a graph showing the change of emission intensity when oxygen is added into the krypton gas and the krypton gas containing nitrogen according to Example 8.

All of the conditions except for the kinds and concentrations of the gas were identical to those of Example 7. The measured results are shown in FIG. 17.

The result shows that if oxygen is mixed, the emission intensity of nitrogen decreases and the sensitivity of nitrogen in krypton is lowered.

The method for compensating the concentration of nitrogen in krypton in the presence of oxygen is provided in the following.

Figure 18:
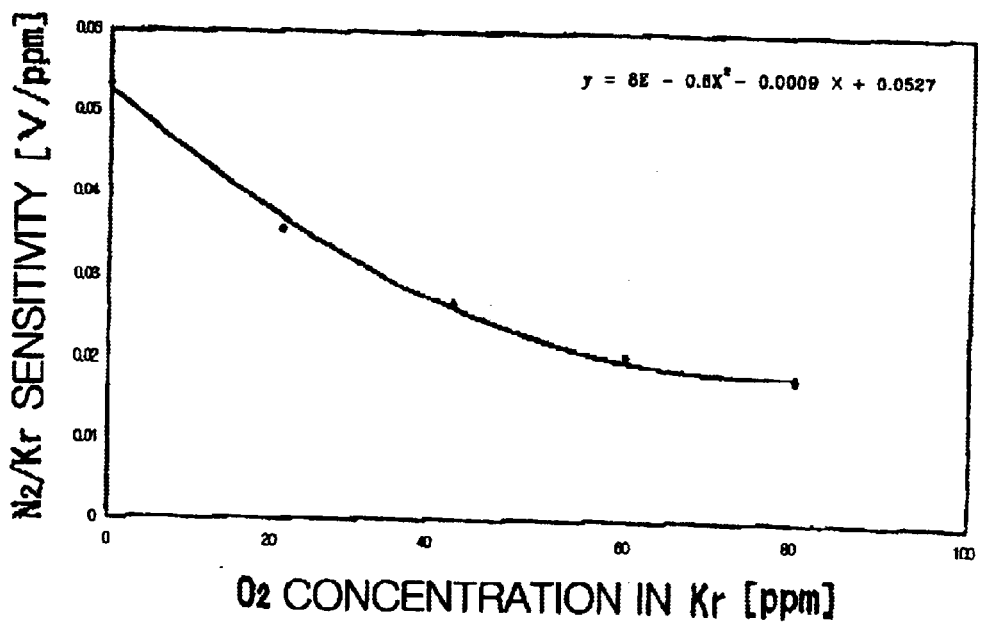
FIG. 18 is a view showing the change of nitrogen sensitivity when oxygen gas is added into the krypton gas and the krypton gas containing nitrogen according to Example 8.

As shown in FIG. 18, the relation between oxygen concentration ($X$[ppm]) and nitrogen sensitivity in krypton ($Y$[V/ppm]) is $Y = 0.00000591X^2 - 0.000905X + 0.0527$.

For example, the sensitivity of nitrogen in krypton can be calculated to be 0.0527[V/ppm] if the oxygen concentration is 0 ppm, and 0.0259[V/ppm] if the oxygen concentration is 40 ppm.

In addition, the relation between the oxygen concentration ($X$[ppm]) and the base line of pure krypton gas ($z$[V]) is $Z = 0.0000351X^2 - 0.00515X + 2.65$. Thus, the base line of the pure krypton gas is 2.65[v] if the oxygen concentration is 0 ppm, and 2.51[V] if the oxygen concentration is 40 ppm.

For example, when 40 ppm of oxygen and 28 ppm of nitrogen are contained in krypton, the output is 3.25V, while the nitrogen concentration calculated from the voltage without correction is $(3.25-2.65) \div 0.0527 = 11.4$[ppm], which is lower than the actual concentration (28 ppm).

However, the nitrogen concentration calculated from the voltage using the correction formula is $(3.25-2.51) \div 0.0259 = 28.6$[ppm], which shows that the nitrogen concentration can be corrected to actual value by measuring the oxygen concentration in a sample gas.

As shown above, the present invention makes it possible to measure the trace amount of nitrogen in various gases with accurate precision in a continuously stable condition.

In addition, as the analysis can be carried out without adding other gases, the costs for analysis can be saved. Further, as the gases after analysis can be reused, the highly expensive krypton gas and xenon gas does not go to waste, helping to save costs for systems using such gases.

What is claimed is:

1. A method for measuring nitrogen in a gas comprising the steps of:
   introducing a sample gas into a discharge tube;
   collecting an emission light generated by discharge;
   extracting a wavelength from the light specific to nitrogen;
   introducing said wavelength to a detector; and
   continuously measuring the concentration of said nitrogen present in said gas according to the intensity of said light detected by said detector,
   wherein, at least one of said wavelengths for measuriug the nitrogen concentration is selected from a group consisting of 215±2 nm, 226±2 nm, 238±2 nm, 242±2 nm, 246±1 nm, 256±2 nm, 260±2 nm, 266±2 nm, 271±1 nm, 276±4 nm, 285±2 nm, 294±1 nm, and 300±2 nm.

2. The method for measuring nitrogen in a gas according to claim 1, wherein said sample gas is a rare gas and selected from a group consisting of
   krypton gas;
   xenon gas;

a mixture of krypton gas and xenon gas;

a mixture of krypton gas and at least argon gas, helium gas and/or neon gas;

a mixture of xenon gas and at least argon gas, helium gas and/or neon gas;

a mixture of xenon gas, krypton gas and at least argon, helium and/or neon.

3. The method for measuring nitrogen in a gas according to claim 1, further comprising the steps of:

initially measuring an emission intensity of a gas without any impurities, the impurities being capable of creating a coexistence effect on the nitrogen measurement, as a standard emission intensity;

comparing the measured emission intensity of said sample gas with said standard emission intensity; and in case said measured emission intensity is smaller than said standard emission intensity beyond a certain extent, determining whether it results from a disorder of the discharge or presence of an impurity or impurities creating a negative coexistence effect.

4. The method for measuring nitrogen in a gas according to claim 3, wherein said impurity or impurities creating a negative coexistence effect is either moisture, oxygen, or a mixture thereof.

5. The method for measuring nitrogen in a gas according to claim 2, wherein said sample gas is krypton.

6. The method for measuring nitrogen in a gas according to claim 2, wherein said sample gas is xenon.

7. The method for measuring nitrogen in a gas according to claim 2, wherein said sample gas is a mixture of krypton gas and xenon gas.

8. The method for measuring nitrogen in a gas according to claim 2, wherein said sample gas is a mixture of krypton gas and at least argon gas, helium gas and/or neon gas.

9. The method for measuring nitrogen in a gas according to claim 2, wherein said sample gas is a mixture of xenon gas and at least argon gas, helium gas and/or neon gas.

10. The method for measuring nitrogen in a gas according to claim 2, wherein said sample gas is a mixture of xenon gas, krypton gas and at least argon, helium and/or neon.

11. An apparatus for continuously measuring nitrogen in a gas, which comprises, in combination:

a discharge tube, means communicating with said discharge tube for introducing a sample gas into said discharge tube, means for collecting emission light generated by discharge from said discharge tube and passing said emission light to a wavelength extracting means, an interference filter means or a spectroscope means for extracting a wavelength specific to nitrogen from said emission light and transmitting at least at least one wavelength selected from a group consisting of 215±2 nm, 226±2 nm, 238±2 nm, 242±2 nm, 246±1 nm, 256±2 nm, 260±2 nm, 266±2 nm, 271±1 nm, 276±4 nm, 285±2 nm, 294±1 nm, and 300±2 nm to a detector, and detector means for receiving said at least one wavelength and continuously measuring the concentration of said nitrogen present in said gas according to the intensity of said light detected by said detector.

12. The apparatus for measuring nitrogen in a gas according to claim 8, wherein the sample gas is rare gas and selected from the group consisting of krypton gas;

xenon gas;

a mixture of krypton gas and xenon gas;

a mixture of krypton gas and at least argon gas, helium gas and/or neon gas;

a mixture of xenon gas and at least argon, helium and/or neon;

a mixture of xenon gas, krypton gas and at least argon, helium and/or neon.

13. The apparatus for measuring nitrogen in a gas according to claim 11, further comprising:

means for initially measuring an emission intensity of a gas which does not include any impurities, the impurities being capable of creating a coexistence effect on nitrogen measuring, as a standard emission intensity;

means for comparing the measured emission intensity of said sample gas with said standard emission intensity; and in case said measured emission intensity is smaller than said standard emission intensity beyond a certain extent, means for determining whether it results from a disorder of the discharge or presence an impurity or impurities creating a negative coexistence effect.

14. The apparatus for measuring nitrogen in a gas according to claim 12, wherein the sample gas is krypton gas.

15. The apparatus for measuring nitrogen in a gas according to claim 12, wherein the sample gas is xenon gas.

16. The apparatus for measuring nitrogen in a gas according to claim 12, wherein the sample gas is a mixture of krypton gas and xenon gas.

17. The apparatus for measuring nitrogen in a gas according to claim 12, wherein the sample gas is a mixture of krypton gas and at least argon gas, helium gas and/or neon gas.

18. The apparatus for measuring nitrogen in a gas according to claim 12, wherein the sample gas is a mixture of xenon gas and at least argon gas, helium gas and/or neon gas.

19. The apparatus for measuring nitrogen in a gas according to claim 12, wherein the sample gas is a mixture of xenon gas, krypton gas and at least argon, helium and/or neon.

* * * * *